US007605710B2

United States Patent
Crnkovich et al.

(10) Patent No.: US 7,605,710 B2
(45) Date of Patent: Oct. 20, 2009

(54) WETNESS SENSOR

(75) Inventors: Martin Crnkovich, Walnut Creek, CA (US); Peter Christensen, Concord, CA (US); Roland Levin, San Ramon, CA (US)

(73) Assignee: Fresenius Medical Care Holdings, Inc., Lexington, MA (US)

( * ) Notice: Subject to any disclaimer, the term of this patent is extended or adjusted under 35 U.S.C. 154(b) by 300 days.

(21) Appl. No.: 11/506,602

(22) Filed: Aug. 18, 2006

(65) Prior Publication Data

US 2008/0041792 A1 Feb. 21, 2008

(51) Int. Cl.
*G08B 21/00* (2006.01)
(52) U.S. Cl. .................. 340/604; 340/603; 340/605
(58) Field of Classification Search .......... 340/604
See application file for complete search history.

(56) References Cited

U.S. PATENT DOCUMENTS

| | | | |
|---|---|---|---|
| 4,583,546 A * | 4/1986 | Garde | 600/371 |
| 4,688,027 A | 8/1987 | Widener | |
| 5,036,859 A | 8/1991 | Brown | |
| 5,045,051 A | 9/1991 | Milder et al. | |
| 5,486,286 A | 1/1996 | Peterson et al. | |
| 6,038,914 A | 3/2000 | Carr et al. | |
| 6,287,273 B1 | 9/2001 | Allers et al. | |
| 6,292,102 B1 | 9/2001 | Smith | |
| 6,384,728 B1 * | 5/2002 | Kanor et al. | 340/573.1 |
| 6,445,304 B1 | 9/2002 | Bandeian, Jr. et al. | |
| 6,461,329 B1 | 10/2002 | Van Antwerp et al. | |
| 6,752,785 B2 | 6/2004 | Van Antwerp et al. | |
| 6,832,507 B1 | 12/2004 | van de Berg et al. | |
| 6,923,782 B2 | 8/2005 | O'Mahoney et al. | |

(Continued)

FOREIGN PATENT DOCUMENTS

AU A-25884/84 9/1985

(Continued)

OTHER PUBLICATIONS

Rhodine, C. N., and Steadman, J. W., "Renal Dialysis Membrane Leak Detector," *ISA Transactions*, 15(3): 233-236 (1976).

*Primary Examiner*—Toan N Pham
*Assistant Examiner*—Kerri L McNally
(74) *Attorney, Agent, or Firm*—Hamilton, Brook, Smith & Reynolds, P.C.

(57) ABSTRACT

The present invention relates to a wetness detector system that rapidly detects the presence of wetness due to a liquid leak in a system. The wetness detector system contains a reusable wetness sensor that is able to accurately detect the presence of wetness and, in the case of an extracorporeal blood treatment, the presence of blood. The wetness detector system can quickly alert both a user and medical personnel that a liquid leak has been detected in a treatment system and, if necessary, halt the removal of liquids and/or blood from the patient. If a liquid leak is not detected for a period of time, the wetness sensor can enter a low power state, extending the life of the device. The wetness detector system can monitor a number of wetness sensors simultaneously, which would, for example, eliminate the need for medical personnel to continuously inspect numerous patients visually for potentially fatal blood leaks due to needle dislodgement during an extracorporeal blood treatment.

24 Claims, 6 Drawing Sheets

U.S. PATENT DOCUMENTS

| | | |
|---|---|---|
| 6,947,131 B2 | 9/2005 | O'Mahoney et al. |
| 6,979,306 B2 * | 12/2005 | Moll ......................... 604/4.01 |
| 7,040,142 B2 | 5/2006 | Burbank |
| 7,084,777 B2 | 8/2006 | Ninberg |
| 7,141,715 B2 * | 11/2006 | Shapira ....................... 604/361 |
| 7,147,615 B2 * | 12/2006 | Wariar et al. ................ 604/6.16 |
| 2002/0198483 A1 | 12/2002 | Wariar et al. |
| 2003/0066340 A1 | 4/2003 | Hassenflug |
| 2003/0128126 A1 | 7/2003 | Burbank et al. |
| 2003/0149349 A1 | 8/2003 | Jensen |
| 2004/0046671 A1 | 3/2004 | Ninberg |
| 2005/0038325 A1 | 2/2005 | Moll |
| 2005/0275547 A1 * | 12/2005 | Kates ......................... 340/605 |
| 2006/0012774 A1 | 1/2006 | O'Mahony et al. |
| 2006/0244616 A1 * | 11/2006 | Hill ........................... 340/604 |
| 2009/0082684 A1 | 3/2009 | Sornmo |

FOREIGN PATENT DOCUMENTS

| | | |
|---|---|---|
| CH | 619563 A5 | 9/1980 |
| DE | 4014572 A1 | 11/1991 |
| JP | 62069136 | 3/1987 |
| JP | 2006055588 | 3/2006 |
| WO | WO 98/38485 A2 | 9/1998 |
| WO | WO 99/24145 | 5/1999 |
| WO | WO 2005/107580 A1 | 11/2005 |
| WO | WO 2006/001759 A1 | 1/2006 |

* cited by examiner

FIG. 6

WETNESS SENSOR

BACKGROUND OF THE INVENTION

Devices for detecting the presence of wetness and/or liquid leaks have a number of applications including in mechanical systems having liquid lines or in experimental protocols or devices in laboratories or in use with those having enuresis or incontinence or those undergoing blood treatments. In particular, it is important to detect wetness due to blood leaks or other liquid line leaks during procedures that involve the removal of blood from a person, procedures like blood donation, blood detoxification, blood filtration/hemofiltration and hemodialysis. In hemodialysis, for example, blood is removed from a patient through a needle into a blood liquid line circuit that carries the blood to a hemodialysis machine that filters out waste toxins and removes excess water from the blood. With blood normally removed from the patient and through the blood liquid line circuit at a rapid rate, dislodgement of the needle or a break in the blood liquid line would lead to rapid and potentially fatal blood loss. For this reason, hemodialysis, which generally takes several hours and must be performed several times a week, is typically done in a medical setting where patients can be supervised. Patients must constantly be monitored visually by medical personnel for blood leaks so that, if needle displacement occurs, it can be identified and remedied before detrimental blood loss takes place.

Many devices have been proposed to detect wetness due to urine or blood or to detect the disconnect of a needle from a patient or a break/leak in a liquid line; however, these devices have several drawbacks. For example, many of the wetness detectors are not particularly efficient and, therefore, are mostly ineffective. Thus, they require too much moisture and/or liquid to trigger an alarm or there is too long of a delay between the occurrence of the wetness and the detection and/or alarm of the wetness. In the case of hemodialysis, these deficiencies could be deadly; quick detection and alert is necessary in order to minimize blood loss due to the disconnect of a needle or a leak in a liquid line. Further, many proposed or existing devices are uncomfortable, unwieldy and, in the case in which an electric circuit is used to detect the moisture, can be unsafe if the patient is not properly protected from the electric circuit. Importantly, many devices are not appropriate to detect blood leaks that occur during extracorporeal blood treatments as the devices either can not distinguish between blood and other bodily liquids or do not do so adequately. Consequently the devices trigger a number of false alarms, a situation that substantially reduces the usefulness of the devices in a medical setting. In addition, many of the known wetness detection devices can not themselves be physically reused, nor are their detection systems designed to be reset after wetness and/or moisture has been encountered.

Thus, there is a need for a wetness detection system that can rapidly detect wetness due to liquid leaks and accurately identify any wetness that may be due to blood, especially in the instance of extracorporeal blood treatments. What is required is a detector that is sensitive enough to detect a small amount of moisture in order to trigger an alert of a liquid leak. There would also be benefit to a wetness detection system that could monitor a number of wetness sensors simultaneously and one that has a number of different alarms at its disposal to alert both users and, where appropriate, medical personnel of blood and/or liquid line leaks. In the case of hemodialysis, this would free medical personnel from having to visually inspect a number of patients for blood leaks due to needle displacement or blood line breaks, allowing them to focus on other tasks. Further, it would be advantageous for the wetness detector to be able to be reused and the wetness detector system be easily reset after wetness has been detected and/or an alarm has occurred.

SUMMARY OF THE INVENTION

The present invention provides for a wetness detector system that can sensitively and quickly detect wetness due to a liquid leak, including blood, and rapidly trigger an alert upon detection of the leak. The wetness detector system can be used in a number of situations and is particularly applicable in detecting a blood leak from the dislodgement of a needle in a patient undergoing an extracorporeal blood treatment and/or a liquid leak from a break in a liquid line of an extracorporeal blood treatment system (e.g., hemodialysis).

Accordingly, the present invention relates to a wetness detector system for detecting a liquid leak comprising a wetness sensor, an attachment device for attaching the wetness sensor to one or more components of the system and a receiver unit in communication with the wetness sensor. The wetness sensor is comprised of a solid support comprising a non-electrically conductive material having first and second surfaces, an electronic transmitter attached to the first surface of the solid support, a trace antenna coupled to the electronic transmitter on the first surface of the solid support, an electric circuit printed on said second surface of the solid support for detecting the presence of wetness, a microcontroller in communication with the electronic transmitter and electric circuit, a power source connected to the microcontroller, electronic transmitter and electric circuit and a voltage detection device coupled to the power source and in communication with the microcontroller for detecting a low power supply of the power source. The receiver of the wetness detection system is comprised of a receiver for detecting a signal transmission from the wetness sensor, a controller in communication with the receiver and an alert system in communication with the controller.

In one embodiment, the electric circuit of the wetness sensor is able to generate a detectable electric signal upon exposure to moisture and based on the measurement of that electric signal, the microcontroller uses a predetermined wetness threshold value and when that value is greater than a specified value, the microcontroller indicates the presence of wetness. In another embodiment, the wetness sensor is attached to an absorbent material surrounding a needle insertion site and is further comprised of an illumination device for detecting the presence of blood, the illumination device connected to the power source and in communication with the microcontroller. In this embodiment, in response to an indication that wetness is present, the microcontroller directs the light emitter to produce either visible or near-infrared light, generating a detectable wavelength that indicates that the wetness present is blood. In both embodiments, the microcontroller directs the wetness sensor to enter a low power state for a specified amount of time when, during a specific interval of time, no electrical signal is measured and/or there is a lack of indication that the wetness present is blood. However, in response to an indication that wetness is present or an indication that the wetness present is blood, the microcontroller directs the electronic transmitter to transmit at least one signal that a liquid line leak or a needle insertion site blood leak has been detected.

In one embodiment, the transmission of the at least one signal of a liquid line or needle insertion site blood leak from the wetness sensor is detected by the receiver of the receiver unit of the wetness detector system. In response to the at least one signal of a blood leak, the controller of the receiver unit triggers the alert system which is comprised of one or more alarms that include the display of a warning message, an audible alarm, a visual alarm and/or a physical alert. In one embodiment, the receiver unit is in communication with one or more wetness sensors wherein each of the one or more wetness sensors transmits unique identification information to the receiver that is recorded by the controller of the receiver unit. In another embodiment, the one or more wetness sensors are further comprised of a wetness sensor receiver and the receiver unit further comprised of a receiver unit transmitter so that there is two-way communication between the one or more wetness sensors and the receiver unit. In this embodiment, the receiver unit can transmit at every specified interval of time a functionality test signal to the one or more wetness sensors and, in response to the functionality test signal, the wetness sensor transmits a signal back to the receiver unit, thereby indicating that the wetness sensor is functional. In a further embodiment, in the instance that the wetness sensor is functional and there is a lack of transmission of at least one signal of a liquid leak from the one or more wetness sensors during a specific interval of time, the receiver unit directs the one or more wetness sensors to enter a low power state for a specified amount of time.

In a particular embodiment, the receiver unit is integrated with a system operational unit and, in a preferred embodiment, the receiver unit is part of the operation unit of an extracorporeal blood treatment system. In this embodiment, in response to the at least one signal of a liquid leak from the wetness sensor, the controller of the receiver unit can also direct the extracorporeal blood system operation unit to stop one or more blood pumps and close one or more liquid line valves of the system. In a preferred embodiment, the extracorporeal blood treatment is hemodialysis and the receiver unit is integrated with a hemodialysis operation unit. In another embodiment, the wetness sensor is further comprised of a reset device that returns the detection status of the wetness sensor to one in which the presence of wetness is no longer indicated. In yet a further embodiment, the alert system of wetness detector system is reset after the controller is instructed by an external operator to halt the one or more alarms, the wetness sensor reset device is triggered and/or moisture is removed from the wetness sensor surface.

In another embodiment, the power source of the wetness detector system is a battery and the microcontroller triggers a low battery alarm when the voltage detected by the voltage detection device is less than a specified voltage. In this embodiment, the low battery alarm would only be triggered in the event of a lack of indication by the wetness sensor that wetness is present. In one embodiment, the low battery alarm is an audible or visual alarm integrated with the microcontroller itself and in another embodiment, the low battery alarm is integrated with the receiver unit/system operation unit and is an audible or visual alarm that differs from the one or more alarms of the alert system. In response to at least one signal transmitted from the wetness sensor that the voltage of the wetness sensor battery is low, the receiver directs the controller to trigger a low battery alarm.

The wetness detection system of the present invention provides for a mechanism to easily, rapidly and accurately detect a liquid leak due to a break in a liquid line of a system or the disconnect and/or dislodgement of a needle from a needle insertion site. The wetness sensor used in the wetness detection system detects the presence of wetness and, when appropriate, determines if the wetness detected is blood, decreasing the number of false alarms typically generated by proposed or current systems and devices. Moreover, the receiver unit of the wetness detection system can communicate with multiple wetness sensors and trigger an alarm if a liquid line or blood leak signal is transmitted from any one of the sensors. Further, the wetness sensor is able to enter a low power mode when wetness and/or blood has not been detected for a period of time, increasing the longevity of the power source of the wetness sensor. The wetness detection system also has a number of safety features. For instance, the receiver unit is capable of communicating with the wetness sensor(s) and determining if the wetness sensors are indeed functional. In addition, the wetness detection system has a low power supply alarm so that when wetness and/or blood has not been detected by the wetness sensor, the device alerts the user and/or medical personnel that the power supply of the wetness sensor will soon require replacing, preventing non-functional wetness sensors from being used. Thus, the wetness detection system allows treatment systems, in particular, extracorporeal blood treatment systems, to be safer overall.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention relates to a system for detecting the presence of wetness, in particular, wetness due to a liquid leak. The wetness detector system is comprised of a wetness sensor, an attachment device for attaching the wetness sensor to the components of the system and a receiver unit in communication with the wetness sensor. The wetness sensor of the wetness detector system is comprised of: a solid support comprising a non-electrically conductive material having a first and second surface, an electronic transmitter attached to the first surface of the solid support, a trace antenna coupled to the electronic transmitter on the first surface of the solid support, an electric circuit printed on said second surface of the solid support for detecting the presence of wetness, a microcontroller in communication with the electronic transmitter and electric circuit, a power source connected to the microcontroller, electronic transmitter and electric circuit and a voltage detection device coupled to the power source and in communication with the microcontroller for detecting a low power supply of the power source.

As used herein, the term "liquid leak" refers to any leak and/or moisture from the liquid-containing/carrying components of a system (e.g., liquid line, reservoir), generally at a site of interface of those liquid-containing components with other components of the system, or at a site at which liquid (e.g., blood, water, insulin, antibiotics) is being removed from or returned to and/or infused into a patient. Thus, a liquid leak could be a liquid line leak and/or a needle insertion site leak, for example. To detect liquid leaks, the wetness sensor can be attached at any point to one or more components of a system. For example, the wetness sensor can be in close proximity to a liquid line entry point/needle insertion site or attached to a material surrounding a liquid line entry point/needle insertion site of a liquid line of the system. The liquid line is preferably a small-sized (e.g., micro-sized) tubing, this type of tubing generally comprised of a polymer (e.g., plastic) having properties (e.g., minimal drag and/or liquid adsorption, non-reactive, non-corrosive, non-degradable) that make it well-suited for carrying the desired liquid. In a particular embodiment, the system is an extracorporeal blood treatment system in which the wetness sensor is attached to various liquid lines of the system to detect leaks in, for example, a hydraulic hose, a line for carrying blood or, in the case of dialysis, a line for carrying dialysate. The wetness sensor attachment device for attaching the wetness sensor to a liquid line, for instance, can be any device that can be attached to the wetness sensor and used to securely attach the wetness sensor to a liquid line of the system including a clasp, coupling, pin, clip, bonding material (e.g., tape, glue) or the like. Preferably, the wetness sensor is positioned/placed at connection interfaces of the liquid line, areas of weakness due to their vulnerability to liquid circulation speed, volume, pressure and wear; thus, these connection areas are more prone to leak and, consequently, represent where many leaks occur.

Figure 1:
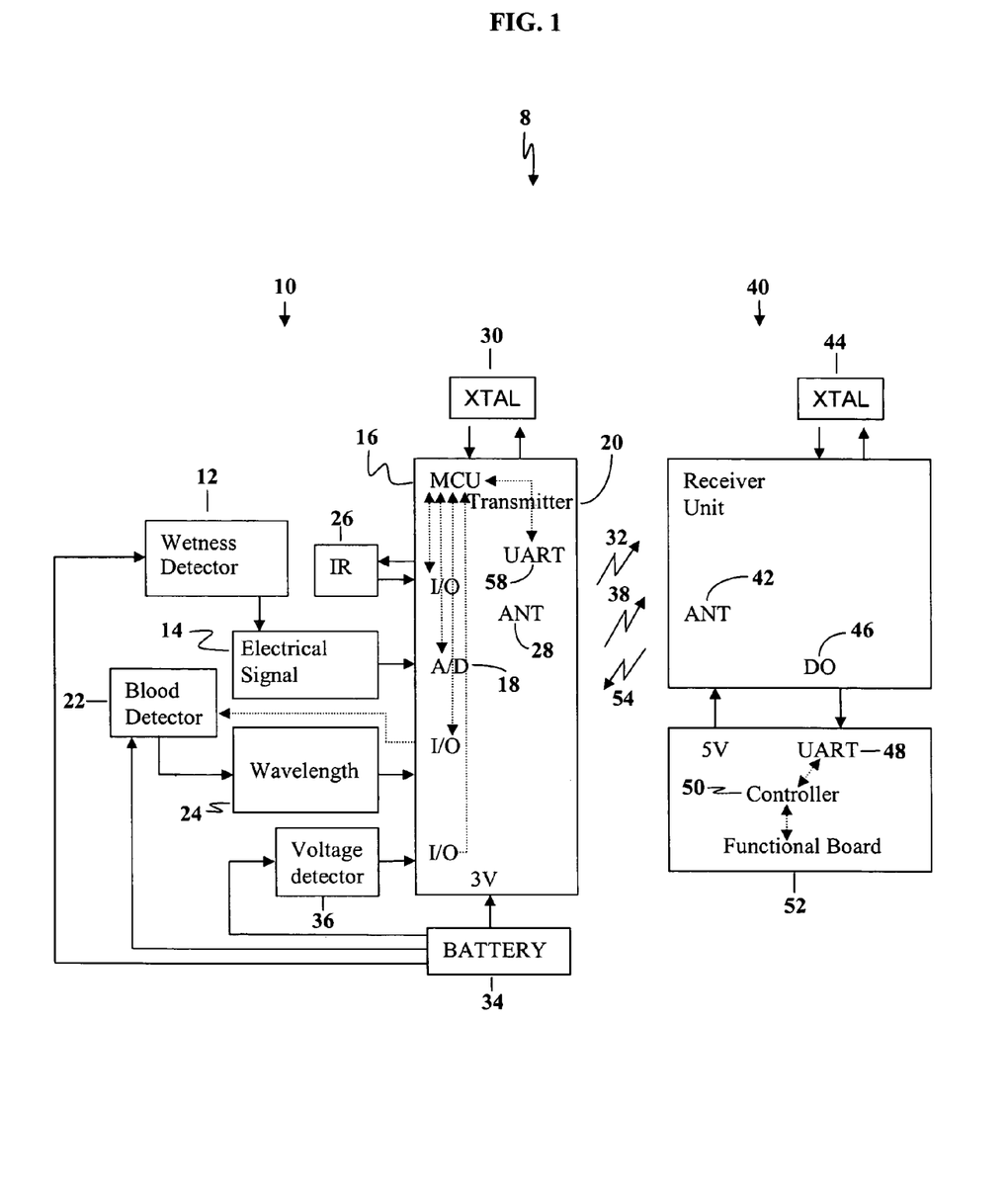
FIG. 1 is a block diagram illustrating a wetness detector system according to the invention.

Accordingly, shown in FIG. 1 is wetness detector system 8 comprised of wetness sensor 10 and receiver unit 40. Wetness sensor 10 of wetness detector system 8 is generally small and preferably watch-sized. Wetness detector 12 of wetness sensor 10 comprises an electric circuit through which moisture/wetness can be detected using the conductivity of the liquid to which the electric circuit is exposed. Thus, the wetness detector system can be used to detect any liquid that is electrically conductive, i.e., contains positively and negatively charged ions that enable the liquid to carry electric current. The electric circuit can be resistive or capacitive so long as the presence of wetness results in a change in the resistance or capacitance of the circuit that is detectable. For example, the circuit could be an open electric circuit wherein the presence of moisture completes the circuit, thereby generating a change in the voltage or current of the circuit that can be detected and measured. In another example, the electric circuit could be in a Wheatstone bridge configuration such that initially the resistance measured across the four resistors of the bridge circuit is equal and/or zero and thus, the bridge is balanced. Exposure of the Wheatstone bridge circuit to the an electrically conductive liquid would alter the resistance of one or more of the resistors comprising the bridge circuit, unbalancing the circuit and generating a detectable change in resistance measured across the electric circuit.

The exposure of the electric circuit of wetness detector 12 to moisture leads to the generation of a detectable electric signal 14 that is sent to microcontroller 16. Thus, wetness sensor 10 is further comprised of analog-digital (AD) converter 18 which digitizes the electrical signal generated by the moisture so that the digital data can be sent/provided to microcontroller 16 for evaluation. Wetness sensor 10 can also include a signal amplifier (not shown) that receives the electric signal and amplifies it to a level that is appropriate for digitization of the signal by AD converter 18. Analog-digital converters (e.g., successive approximation, dual-slope integrating, charge balancing, flash) are well-known in the art and a number of considerations (e.g., resolution, linearity, sample and hold acquisition time, throughput, integration time, recalibration ability) can be taken into account by the skilled artisan in choosing the converter most appropriate for use in a particular wetness sensor. A filter (e.g., bandpass, anti-aliasing) can also be used in sensor 10 to decrease the aliasing introduced into the signal by AD converter 18. A number of both signal amplifiers and filters are well-known to the skilled artisan and are commercially available. The electric circuit can also be connected to a device that measures the electric signal including, for instance, a voltmeter, galvanometer, electrometer, ammeter or ohmmeter. For example, in the embodiment in which the electric circuit is resistive, microcontroller 16 determines that wetness is indicated when exposure of the circuit to moisture generates a detectable change in resistance across the electric circuit that measures, for example, between about 0.3 and 3 Megohms (M ohms).

Microcontroller (MCU) 16 of wetness sensor 10 receives the digitized data of 30 the electric signal generated by wetness detector 12. Microcontroller 16 can be any that meets the general specifications of an MCU, that is, one that contains all the necessary functional components of a computer (e.g., central processing unit (CPU) core, program memory (ROM or flash), data memory (RAM), external peripherals, complementary resource and input/output (I/O) interfaces to communicate with the peripherals). Microcontroller architectures are commercially available from a number of sources (e.g., IBM/AMCC, Atmel, Cypress MicroSystems, Freescale Semiconductor, Fujitsu, Holtek, Hitachi, AVR, Infineon, Intel, Microchip, National Semiconductor, Texas Instruments, Toshiba, others). Based on the measurement of the electric signal generated, microcontroller 16 determines a wetness threshold value from the AD converter value wherein a wetness detection threshold value above a specified value indicates the presence of wetness. One having skill in the art can specify the appropriate threshold value at which microcontroller 16 determines that the moisture to which the wetness detector has been exposed meets the criteria of "wetness" based on the particular microcontroller parameters and the desired sensitivity of detection (e.g., for a particular liquid and/or patient(s)). Preferably, the electric circuit of the wetness detector can detect as little as 5 cubic centimeters (cc) of liquid in order to signal that a liquid leak has occurred.

Wetness sensor 10 can be further comprised of a blood detector 22 that includes an illumination device for detecting the presence of blood. In a particular embodiment, wetness sensor 10 identifies a blood leak associated with the dislodgement/displacement of a needle used in removing and/or returning blood to a patient during an extracorporeal blood treatment. Thus, wetness sensor 10 is preferably attached to an absorbent material surrounding a needle insertion site such that it is in close enough proximity to the site to quickly detect any wetness due to blood that has leaked from the site. Preferably, the wetness sensor is within a few centimeters of where the needle has been inserted in a patient's vein and/or artery. The material surrounding the needle insertion site can be any absorptive material (e.g., absorbent pad, foam, cloth, paper) appropriate for medical use (e.g., sterile) and preferably, would be a sterile wound dressing (e.g., gauze, mesh, band-aid).

The illumination device of blood detector 22 is connected to power source 34 of wetness sensor 10 and is also in communication with microcontroller 16. The illumination device can be comprised of a light source that produces/emits light in the visible or near-infrared spectrum, both types of light allowing for the specific identification of the moisture present. In one embodiment, the illumination device of blood detector 22 is on constitutively, emitting light at some constant interval (e.g., every 10 seconds). Alternatively, blood detector 22 could be electrically connected to wetness detector 12 (e.g., part of the electric circuit), such that the electric signal generated by the moisture present turns on the light source the illumination device of blood detector 22. In a particular embodiment, in response to an indication of wetness, microcontroller 16 directs the illumination device light source to emit light in order to determine if the wetness present is blood. The light emitted by the light source allows for the specific identification of the moisture present due to differing structural properties of different molecules. Thus, different molecules absorb light at distinct wavelengths and, consequently, knowledge of the absorbance spectrum of a particular molecule and/or substance allows for that substance to be identified by its spectral signature. Accordingly, the absorbance spectrum of the primary light-absorbing molecules of blood, oxyhemoglobin and deoxyhemoglobin, is known, making wetness due to blood distinguishable from wetness due to some other electrically conductive liquid (e.g., sweat). The illumination device of blood detector 22 can produce light using any appropriate light source (e.g., a halogen or tungsten lamp), and preferably produces visible light or near-infrared light using a light-emitting diode (LED), so long as the light source produced is safe for use on humans (see Duchlne A S, et al., *IRPA Guidelines on Protection Against Non-ionizing Radiation.* Toronto, Ontario, Canada, Pergamon Press Canada, Ltd. 1991, pg. 53-66). Light emitted by the illumination device of blood detector 22 and absorbed by the moisture present causes the generation of a detectable wavelength 24 that is captured by a wavelength-calibrated photodiode. The wavelength 24 detected and captured by the photodiode is received by microcontroller 16. In the case of blood detector 22, upon the generation of a wavelength measuring between about 520 nanometers (nm) and 610 nm due to the absorbance of visible light by the moisture present, or between about 740 nm and 820 nm due to absorbance of near-infrared light by the moisture present, microcontroller 16 would determine that the moisture to which wetness detector 12 has been exposed and/or the wetness that has been detected is blood.

In the instance that wetness and/or blood is not detected by wetness sensor 10 for a specified period of time, microcontroller 16 can direct wetness sensor 10 to enter a low power state, thereby elongating the life of the power source of wetness sensor 10. Thus, when there is a lack of electrical signal 14 and/or wavelength measurement 24 for a specified amount of time, microcontroller 16 causes wetness sensor 10 to enter a low power state for a specific interval of time, the specified amount of time and specific interval of time measured by a clock internal to and/or associated with microcontroller 16. The amount of time that elapses without wetness and/or blood detection before the wetness sensor enters a low power state and the interval of time the wetness sensor remains in a low power state is best determined by one having skill in the art, these time periods alterable through the programming of microcontroller 16. For instance, the skilled artisan could alter the time periods (e.g., before entry into a low power state and the duration of the low power state) according to field testing or based on use of the wetness sensor in clinical practice. The ability of wetness sensor 10 to enter a low power state can be due to several actions including reducing power to the electric circuit of wetness detector 12, microcontroller 16 (e.g., by halting the execution of non-essential MCU functions) and/or blood detector 22 if the illumination device of blood detector 22 turns on at regular intervals without an electrical signal and/or direction from microcontroller 16. In another embodiment, if the wetness detected by wetness detector 10 is not blood, then, during a low power state, the wetness can safely be eliminated from the surface of the electric circuit, thereby eliminating the non-blood wetness source and any electric signal being generated by that wetness.

Wetness sensor 10 is also comprised of transmitter 20 connected to antenna 28, transmitter 20 generating and/or modulating a signal wave that transmits a liquid leak signal to receiver unit 40. Thus, in response to an indication of wetness and/or an indication that the wetness present is blood, microcontroller 16 directs transmitter 20 to send a signal 32 via antenna 28 that a liquid leak has been detected by wetness sensor 10. The liquid leak signal transmission encompasses a communication that includes not only the signal of a liquid leak, but also other pertinent information (e.g., wetness detection signal, wavelength value, power levels, sensor functionality); alternatively, the data stream containing other information can be transmitted separately. Transmitter 20 can be any appropriate transmitter (e.g., amplitude-shift key (ASK)) and can also be separate from microcontroller 16. However, in a preferred embodiment, the microcontroller and transmitter are integrated into one functional unit (e.g., rfPIC12F675F). In this case, the microcontroller can have an external crystal to generate transmission frequencies (e.g., 13.56 MHz).

In order to send a signal of a liquid leak to receiver unit 40, wetness sensor 10 can be wired to receiver unit 40 such that liquid leak signal 32 is transmitted to a receiver unit 40 over hardwire(s). In a particular embodiment, blood leak signal 32 is transmitted to receiver unit 40 wirelessly with the data encoded for wireless transmission (e.g., using pulse width modulation). Wireless communication can be through any suitable wireless data network or can be through a wireless communication link (e.g., Bluetooth, ZigBee). Overall, any wired or wireless data transmission network can be used for communication between the wetness sensor and the receiver unit. Accordingly, in response to an indication that the wetness sensor has been exposed to wetness and/or blood, transmitter 20 generates a signal wave in the near-infrared band using infrared (IR) device 24. Preferably, the infrared signal can then radiate and propagate liquid leak signal 32 by antenna 28 over a selected frequency to receiver unit 40. Crystal oscillator 30 creates a precise, stable frequency over which liquid leak signal 32 can be transmitted and typically resonates at some standard frequency (e.g., 10, 20, 40 MHz); however, in a preferred embodiment the crystal oscillator transmits at a frequency of 433.92 MHz. Crystal oscillators (XO) can be further used as a precise clock to enable a particular type of signal transmission (e.g., synchronous serial transmission or asynchronous transmission) from wetness sensor 10 to receiver unit 40. There are numerous types of crystal oscillators that can be used in the wetness detector system (e.g., microcomputer-compensated (MCXO), oven-controlled voltage-controlled (OCVCXO), oven-controlled (OCXO), rubidium (RbXO), temperature-compensated-voltage controlled (TCVCXO), temperature-compensated (TCXO) and voltage controlled (VCXO)). The type of signal transmission (e.g., continuous or idle) is best chosen by one having skill in the art as being most appropriate for the conditions of use and is preferably one that complies with industry standards (e.g., RS232-C, CCITT). It is preferable that the crystal oscillator design reduce environmental effects (e.g., temperature, humidity, pressure and vibrations) for better frequency stability. The duration of the signal transmission can be any desirable length and in a particular embodiment, the duration of the signal transmission is 100 milliseconds (msec). At least one signal that a liquid leak has been detected can be transmitted at every specified interval of time dependent, for instance, on the length of signal transmission. In a preferred embodiment, two signals in a row are transmitted every 60 seconds which could also distinguish the two liquid leak signals from other baseline and/or other data transmissions. In order to quickly alert a user (e.g., subject, patient and/or medical personnel) that a liquid leak has occurred before significant liquid loss, particularly blood loss, can take place, it is envisioned that wetness sensor 10 detects wetness and, if necessary, identifies that wetness as blood and transmits the signal of a liquid leak to a receiver unit within a few seconds of an indication that wetness and/or blood is present.

Receiver unit 40 of wetness detection system 8 that receives the liquid leak transmission from wetness sensor 10 is comprised of a receiver for detecting a signal transmission from the wetness sensor, a controller in communication with the receiver and an alert system in communication with the controller. Receivers are commercially available, for example, MICFO22BM from Micrel. Thus, antenna 42 of receiver unit 40 receives liquid leak signal transmission 32 from wetness sensor 10 that a liquid leak has been detected over a matching frequency (e.g., 433.92 MHz) that is generated by crystal oscillator 44 of receiver unit 40. Data output interface (DO) 46 on the receiver provides to controller 50 the data which is transmitted from wetness sensor 10 to the receiver. In one embodiment, receiver unit 40 can be in communication with one or more wetness sensors. In this case, wireless communication/signal transmission between the one or more wetness sensors and the receiver unit is most advantageous. In order for the receiver unit to accurately monitor transmissions from more than one wetness sensor, it would be necessary for each wetness sensor to transmit unique identification information, typically a unique identification (ID) number stored in the microcontroller memory (e.g., dynamic random access memory (DRAM), static random access memory (SRAM), electrically erasable programmable read only memory (EEPROM) or other storage medium(s)), the ID transmitted to receiver unit 40. Receiver unit 40 would then, in turn, need to be comprised of a device and protocol to learn, store and track this unique ID information (e.g., an appropriately programmed microcontroller). Preferably, the alert system for each wetness sensor would be reset when the receiver unit initially receives transmission of a unique ID from each of the wetness sensors. To perform its various functions, receiver unit 40 would either be connected to a power source (e.g., AC or DC) or further comprised of a battery. Alternatively, receiver unit 40 could be integrated with a system like an extracorporeal blood system operation unit which performs various blood treatment functions (e.g., blood oxygenation, detoxification, transfusion or filtration). Thus, controller 50 would be a central computer controlling the system of the extracorporeal blood treatment unit including functional board 52 of the system unit. In this case, the receiver unit would be powered by the power source of the extracorporeal blood treatment system unit and interface with the system controller. In a preferred embodiment, the receiver unit of the wetness detector system is integrated with a hemodialysis treatment system unit.

Accordingly, in response to at least one signal transmission 32 from at least one wetness sensor 10 that a liquid leak has been detected, controller 50 (e.g., one or more computer processors) receives the signal communication from the receiver DO 46 via universal asynchronous receiver-transmitter (UART) 48, the UART microchip providing an interface for the controller to the receiver. Thus, UART 48 receives serial bits of data from the receiver and converts the bits into complete bytes that are interpretable by controller 50. A number of UART devices are available (e.g., 8250, 16550) and it is preferable that the UART provides some amount of buffering of the data (e.g., 16550 UART) so that the data can be cached, reassembled and reorganized before being sent to the controller. Controller 50 can then trigger the alert system indicating that a liquid leak has been detected by a particular wetness sensor. For example, controller 50 can deliver a warning message that is displayed either on the receiver unit (if distinct) or on the functional board of an extracorporeal treatment system operation unit, for instance. In addition, controller 50 can trigger one or more alarms that are audible, visual or physical. The alarms can be any known audible (e.g., a high volume sound, bell, siren, horn, buzzer, beep, whistle, recording or voice) or visible (e.g., colored, flashing, strobe, fluorescent or halogen light) alarm. If the wetness detector system is used to detect liquid leaks in some sort of treatment system (e.g., an extracorporeal blood treatment system), a physical alarm can also be employed to warn the patient/user. For instance, the controller can cause a blood pressure cuff attached to a patient's arm to squeeze the patient's arm, thereby waking and/or alerting the patient. Similarly, a device capable of vibration could be attached to a patient (e.g., on a blood pressure cuff) and the controller could cause the device to vibrate rapidly and/or audibly so that the user would be alerted.

In another embodiment of wetness detector system 8, wetness sensor 10 can be further comprised of a receiver (sensor receiver) and receiver unit 40 can be further comprised of a transmitter (receiver transmitter) such that there can be two-way communication between the wetness sensor and the receiver unit. Two-way communication between the receiver unit and the wetness sensor is advantageous as it allows the receiver unit to send a number of communications to the wetness sensor(s) including software updates, inquiry into configuration settings, reconfiguration of sensor settings and/or determination of the number of times the wetness sensor has been used. Further, as one-way signal transmissions from the wetness sensor to the receiver unit can be easily interrupted by interference from other devices, particularly in a medical setting, two-way communication can be utilized to ensure that liquid leak signal transmissions from the wetness sensor(s) are received by the receiver unit. Thus, the receiver unit could transmit an acknowledgement communication back to the wetness sensor after it has safely received a liquid leak signal transmission. In addition, two-way communication would be useful in enabling the receiver unit to ascertain if the wetness sensor is functional. Accordingly, in one embodiment, a transmitter of receiver unit 40 sends a functionality inquiry test signal 54 to at least one wetness sensor 10 at every specified interval of time (e.g., every 60 seconds). Functionality test signal 54 is received by a wetness sensor receiver and the data converted by UART 58 for microcontroller 16. In response to functionality test signal 54, microcontroller 16 of an operational wetness sensor 10 directs the wetness sensor transmitter to send a functionality confirmation signal back to receiver unit 40, the transmission of the signal indicating to the receiver unit that the wetness sensor is functional. The number of such communications can be varied (e.g., two or more transmissions) per specified interval of time. Preferably, wetness sensor 10 would also retain an ability to receive the functionality test signal 54 and transmit a functionality confirmation signal in response while in a low power mode that has been initiated by microcontroller 16 (e.g., in response to a lack of an electric signal and/or blood detection). Two-way communication could also allow receiver unit 40 to direct one or more wetness sensor(s) 10 to enter a low power state. Thus, if there has been no transmission of a liquid leak signal from wetness sensor(s) 10 for a specific interval of time (e.g., 2.5 minutes) and receiver unit 40 has received a functionality confirmation signal from wetness sensor(s) 10, then receiver unit 40 could transmit a signal to wetness sensor(s) 10 directing the one or more wetness sensor(s) to enter a low power state for a specified amount of time (e.g., 15 seconds).

Advantageously, the alert system of wetness detector system 8 can easily be reset after one or more alarms have been triggered by the wetness sensor(s), one or more alarms that include the display of a warning message, triggering of visible, audible or physical alarms, or the stopping of the extracorporeal blood treatment via the halting of blood pump(s) and/or closing of liquid line valves. Thus, wetness sensor 10 can be further comprised of a reset device that returns the sensor to a state in which microcontroller 16 does not perceive and/or indicate the presence of existing and/or past wetness. This feature would be most useful when, for example, the wetness sensor is used to detect a blood leak at a needle insertion site and the wetness detected by the sensor is some other liquid (e.g., sweat) that is not blood. In a further embodiment, the wetness sensor could be reset by the receiver unit if two-way communication is employed. In this case, an external operator (e.g., medical personnel) could, through an input device that is on (e.g., dials, buttons, keys, switches or the like) or in communication with (e.g., a remote) receiver unit 40 and/or functional board 52, direct controller 50 to transmit a signal to wetness sensor 10 that instructs microcontroller 16 to reset any indications of wetness and/or blood. In another embodiment, wetness sensor 10 can be programmed such that if the wetness detector system is reset a specified number of times (e.g., three times) within a specific amount of time (e.g., ten minutes), then, in the event of any subsequent liquid leak signals, the full alert system is not triggered. Instead, the next liquid leak signal causes the display of a warning message only on the receiver unit/treatment system. Wetness sensor 10 could also be reset by the user or any medical personnel through the direct removal of the moisture from the sensor surface, by wiping the sensor with an absorbent material, for example.

Wetness detector system 8 also has a number of safeguards to ensure wetness detector 10 is able to detect wetness and/or blood or has adequate power to do so. For instance, before being used on a patient, the wetness sensor can be self-tested, preferably after its initial location and/or identification by the receiver unit. Thus, upon the touching of the electric circuit of wetness sensor 12 by an external operator, wetness sensor 12 would send an initial signal to a receiver that the electric circuit and thus, wetness sensor 12, is functional for wetness detection. Generally the circuit of the wetness sensor would initially detect wetness and functionality due to the natural moisture of the external operator (e.g., medical personnel or user). In response to this initial signal from wetness sensor 12, the receiver unit 40 would preferably display a message on the receiver unit and/or extracorporeal blood system operation unit that the wetness detector(s) is functional. Further, to alert a patient and/or medical personnel of a limited energy status of the wetness sensor power source (e.g., less than 10% of the life of a battery), wetness sensor 10 can be further comprised of a low power alarm circuit. Thus, the power source of wetness sensor 10 is battery 34, (having 3 volts), which is connected to voltage detector 36, the voltage detector in communication with microcontroller 16. When the voltage measured by voltage detector 36 is less than a specified voltage (e.g., 2.2 volts), microcontroller 16 triggers a low battery alarm. A low battery alarm would only be triggered in the instance that the presence of wetness is not also indicated by the wetness sensor. The low battery alarm can be an audible and/or visual alarm located on the wetness sensor itself or integrated with the receiver unit and/or an extracorporeal blood treatment system unit. In the case that the alarm is located on the wetness sensor, the audible alarm could be a sound produced by microcontroller 16 and the visual alarm could be a small, low-powered LED directed to be turned on by microcontroller 16. Alternatively or in addition to any alarm on the wetness sensor itself, microcontroller 16 can direct the transmission of one or more signals 38 to receiver unit 40 that the voltage of battery 34 is low. In response, controller 50 of receiver unit 40 can display a warning message and/or trigger one or more visual or audible alarms. Preferably, the low battery warning message and alarm(s) differ in text, sound, volume and/or intensity from the one or more alarms of the liquid leak alert system.

Figure 2:
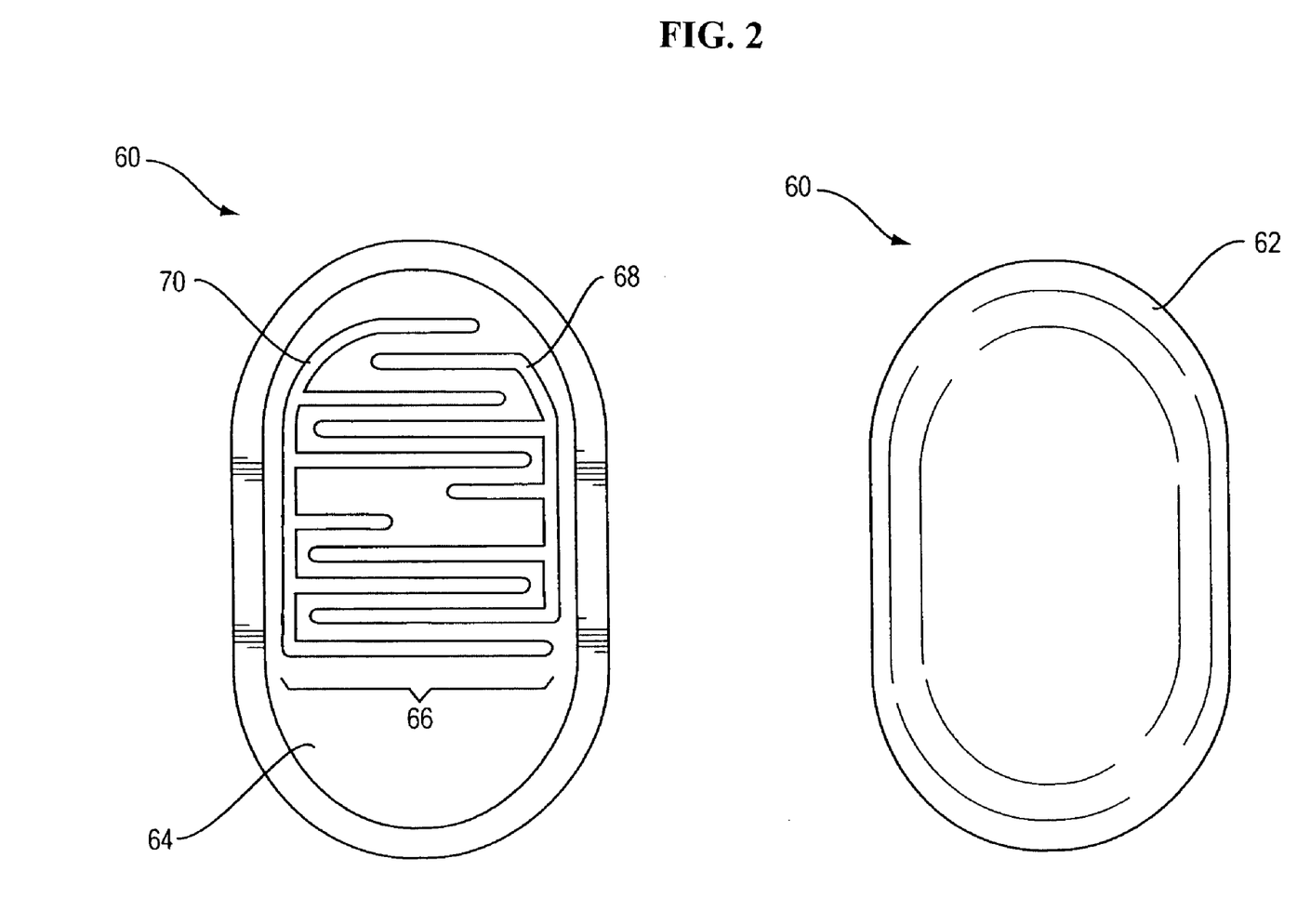
FIG. 2 is a photograph of a prototype of a wetness sensor according to the invention.
Figure 3:
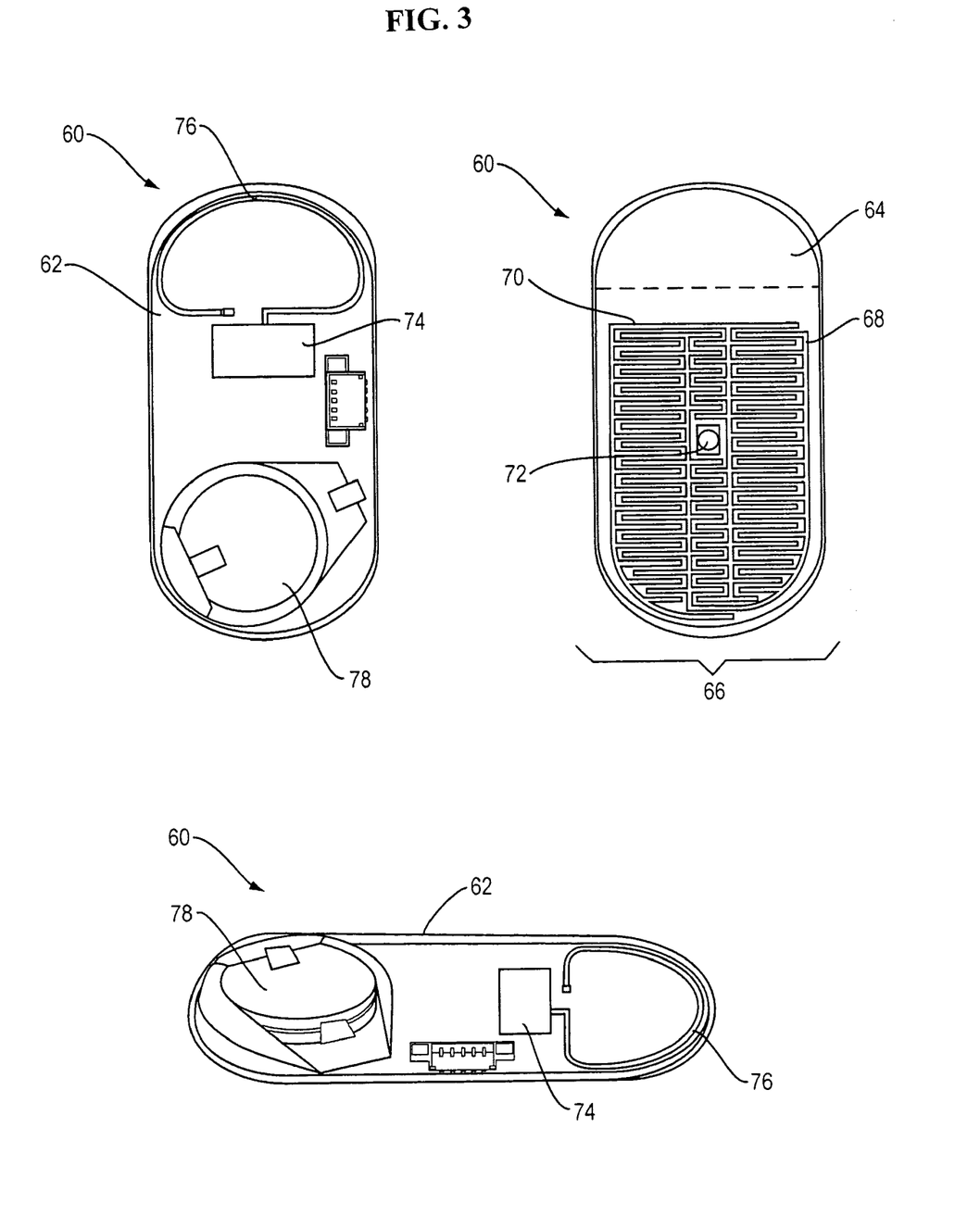
FIG. 3 is a schematic illustrating a wetness sensor for use in a wetness detector system according to the invention.

A prototype of a wetness sensor device, featuring an open electric circuit as described is shown in FIGS. 2 and 3. Wetness sensor 60 is comprised of a solid support having first side 62 and a second side 64 and can be activated and/or turned on by an initial touching of the electric circuit on the second side of the wetness sensor. The solid support comprising the wetness sensor generally would be a material that does not conduct electricity (e.g., an insulator) and, in a particular embodiment, is a potting compound (e.g., FR-4, a resin reinforced with a woven fiberglass mat) that holds the components of the sensor and/or makes up the sensor bulk surrounding sensor components and, if desired and/or necessary, can include a thermally conductive layer between sensor components to dissipate heat (e.g., heat generated by the electric circuit). On second side 64 of wetness sensor 60, electric circuit 66 contains electrode 68 and electrode 70, the electrodes (i.e., anode and cathode) interwoven through the use of interdigitating electrode fingers. This design involving the interdigitation of electrode fingers more easily allows any moisture to which the electric circuit is exposed to close/bridge the gap between the electrodes and thus, more easily complete the electric circuit and/or generate a detectable electric signal. The material that makes up the electric circuit can be any electrically conductive material including a metal (e.g., silver, gold, copper, tin nickel, lead, aluminum), a polymer (e.g., plastic), silicon or carbon. The electric circuit could be excited/powered by any AC or DC power source that produces enough power such that a change in voltage or current due to the presence of moisture can be detected. Preferably, the power source is small enough to fit inside the wetness sensor itself.

A detailed schematic of wetness sensor 60 is shown in FIG. 3. For the detection of wetness, electric circuit 66, printed on second surface 64, is as described previously, that is, comprised of interdigitating electrode fingers 68 and 70. Also, attached to second surface 64 is illumination device 72 comprised of a light source appropriate for the identification of the wetness as blood. Electric circuit 66 and illumination device 72 could be covered by a porous material (e.g., an encapsulant/potting material) that allows moisture/liquid through, yet insulates a subject/patient from any electric signal generated. Such encapsulants are known in the art and typically include polymers like polyolefin, polyvinylchloride, polyester, polyurethane, elastomer and synthetic rubber. Attached to first surface 62 of wetness sensor 60 is microcontroller/transmitter unit 74 and trace antenna 76. Although several types of antennas could be used to transmit a blood leak signal, it is preferable that the antenna be electrically small (e.g., physically small with respect to wavelength) and, most preferably, be a printed circuit board (PCB) loop antenna as embodied by trace antenna 76. A battery 78, acting as a power source for wetness sensor 60, is also within the device. The battery for use in the wetness sensor of the invention can be a wide variety of batteries (e.g., lithium, lithium ion, nickel cadmium, zinc carbon, alkaline, nickel metal hydride, nickel iron, nickel zinc or specialty battery) and is best selected by the skilled artisan for the particular design and usage of the wetness sensor. In a preferred embodiment, the battery is a coin-sized lithium battery (e.g., CR2032) as these types of batteries are small, long-lasting, light-weight and have higher, more stable voltage profiles.

Figure 4:
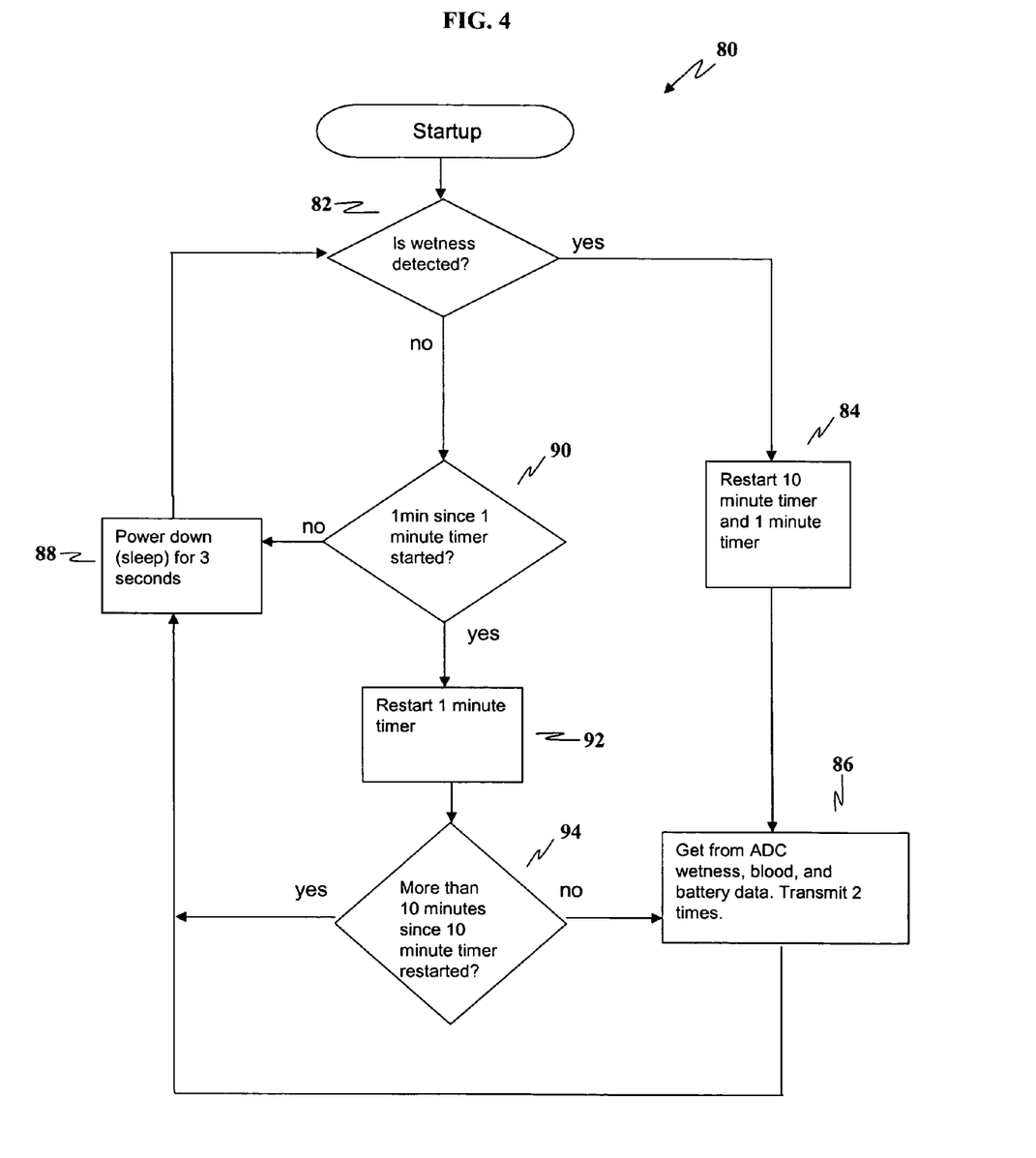
FIG. 4 is a flow diagram illustrating the operation of a wetness sensor.

Depicted in FIG. 4 is a flow chart illustrating an example of processing performed by microcontroller 16 of wetness sensor 10 that includes entry of the wetness sensor into a low power state, as described previously. Process 80 begins with decision block 82 in which microcontroller 16 determines if an electric signal has been generated. An electric signal indicates that wetness/blood has been detected (i.e., through comparison to a wetness detection threshold value). If wetness/blood has been detected, process 80 proceeds from decision block 82 to block 84 in which microcontroller 16 restarts two timers; one timer set for 10 minutes (10 minute timer) and another set for 1 minute (1 minute timer). When wetness/blood has been detected and the 10 minute and 1 minute timers have been reset, in block 86 microcontroller 16 transmits a data transmission twice in a row indicating both that wetness/blood has been detected and the energy level status of the battery. After transmission of this information in block 86, wetness sensor 10 powers down (sleeps) for 3 seconds, after which process 80 returns to decision block 82. If wetness/blood is not detected in decision block 82, then process 80 proceeds to decision block 90 in which microcontroller 16 determines the status of the 1 minute timer. Thus, in decision block 90, if 1 minute has not passed since the 1 minute timer was started then microcontroller 16 directs wetness sensor 10 to power down for 3 seconds. Alternatively, if in decision block 90 1 minute has not elapsed since the 1 minute timer was started, then process 80 proceeds to block 92 in which the 1 minute timer is restarted and then to decision block 94 in which microcontroller 16 determines if more than 10 minutes have elapsed since the 10 minute timer was restarted. If, in decision block 94 ten minutes have elapsed since the 10 minute timer was restarted, then microcontroller 16 has wetness sensor 10 power down for 3 seconds in block 88 and return to decision block 82. If, instead, more than 10 minutes have not elapsed since the 10 minute timer was restarted, then microcontroller 16 again transmits a data transmission twice in a row indicating both that wetness/blood has been detected and the energy level status of the battery and then directs wetness sensor 10 to enter a low power state for 3 seconds in block 88. This process using the two timers allows the wetness sensor to continue to send messages for a short amount of time after wetness is no longer present, telling the receiver that the wetness condition has been cleared and allowing the wetness sensor to send a low battery signal even in the event that a wetness signal is not also being transmitted. Importantly, process 80 directs the wetness sensor to transmit a wetness signal every 3 seconds, ensuring that such a signal would not be missed (e.g., by medical personnel).

Figure 5:
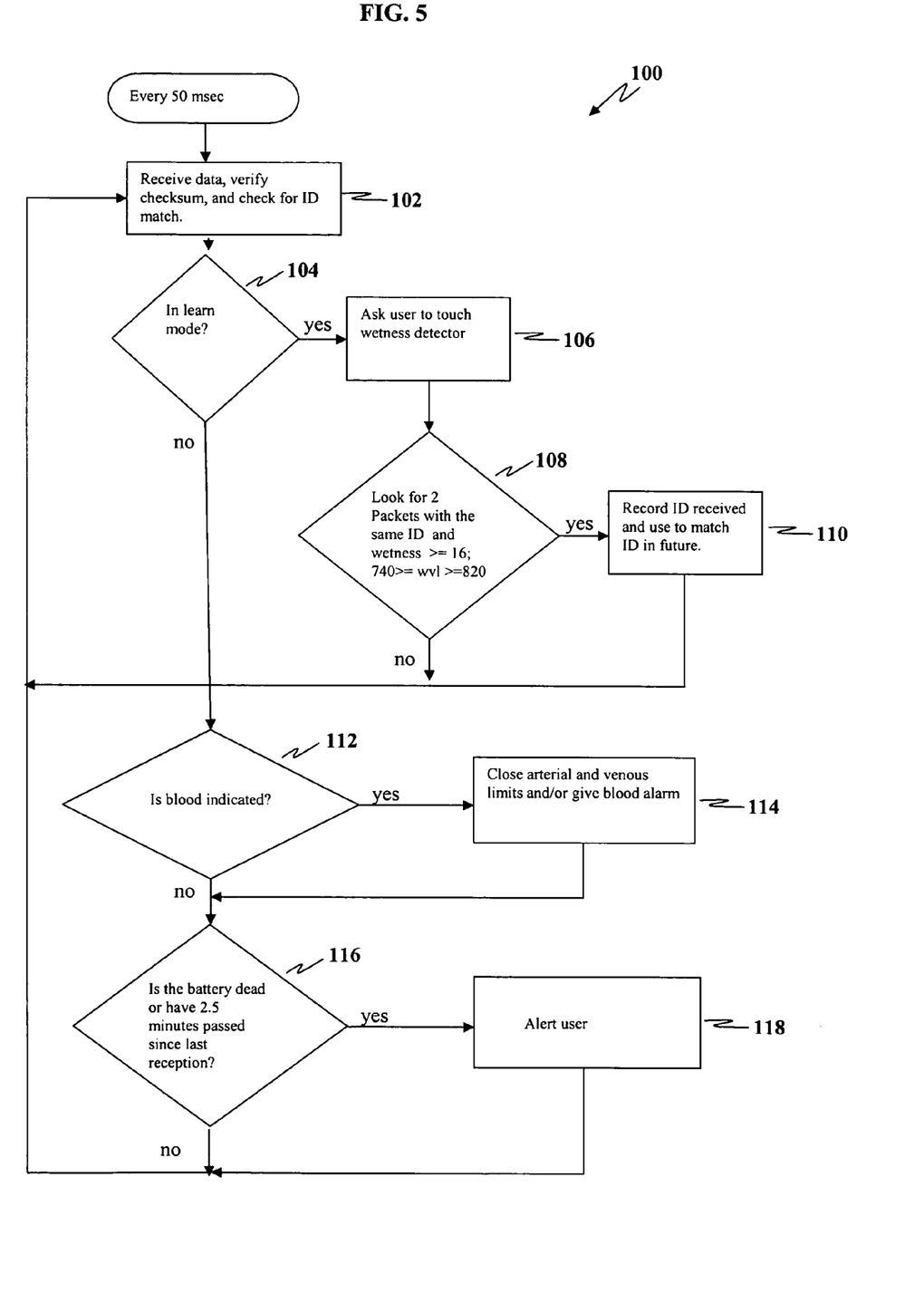
FIG. 5 is a flow diagram illustrating the operation of a receiver unit in response to the detection of a blood leak by a wetness sensor.

The operation of a controller in response to detection of a blood leak by a wetness sensor during an extracorporeal blood treatment could occur as illustrated in a flow diagram of process 100 in FIG. 5. In process 100, every 50 msec receiver unit 40 would receive data transmitted from wetness sensor 10 and controller 50 would determine if the identification data (ID) sent by the wetness sensor is known in block 102. In decision block 104, the controller would determine if it is in a learning mode and, if the controller is in a learning mode, would direct the user/medical personnel (by display of a message on the receiver/system unit) to touch the wetness sensor face (e.g., electric circuit) for self-test in block 106. In decision block 108, controller 50 would then determine if the same wetness sensor has sent two signals that wetness has been detected (i.e., a wetness detection threshold above a specified value (16)) and that the wetness is blood (i.e., a wavelength detected that indicates the presence of blood (between 740 and 820 nm)). If two liquid leak signals have been received from the same wetness sensor ID, then controller 50 records the ID received to use to match in a future signal transmission in block 110. Alternatively, if signal of a liquid leak has not been received from the same wetness sensor ID, process 100 proceeds back to block 102 to verify that two signal transmissions of a blood leak have been received from the same wetness sensor ID. Based on the information in block 102, in decision block 104 controller 50 would determine if, for the wetness sensor ID, it is in learning mode (e.g., the wetness sensor ID is known) and, if not, process 100 would proceed to decision block 112 to determine if the wetness sensor has detected wetness (e.g., blood). If the controller determines that blood is indicated by the wetness sensor, then the controller triggers one or more alarms and/or stops the blood pump and closes arterial and venous valves in block 114. If controller 50 determines that blood is not indicated in decision block 112, the controller ascertains if the wetness sensor is functional (e.g., has power or has sent a recent transmission) in decision block 116. If the wetness sensor is not functional, controller 50 alerts the user in block 118. Alternatively, if the wetness sensor is functional, the controller would return to the beginning of process 100 at block 102 upon the next reception of a signal from a wetness sensor.

Figure 6:
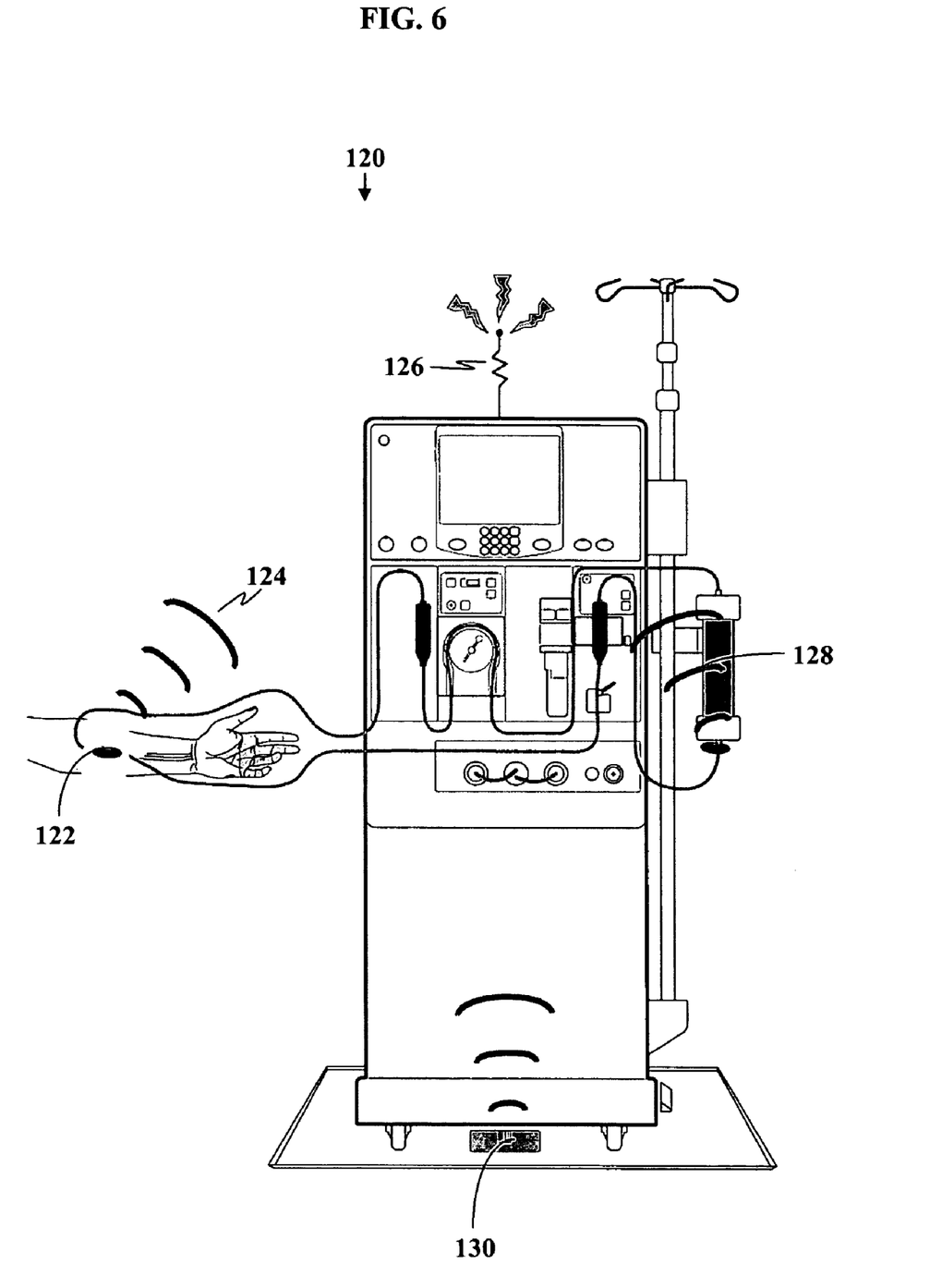
FIG. 6 is a schematic illustrating a wetness detector system in which the receiver unit is integrated with a hemodialysis system operation unit.

Thus, in a particular embodiment shown in FIG. 6, wetness sensor 122 is attached to a wound dressing covering a needle insertion site and signal 124 of a blood leak is transmitted through wires 128 or wirelessly via antenna 126 to a receiver unit integrated with the hemodialysis treatment operation unit 120. In this embodiment, transmission of a blood leak triggers an audible alarm 130 that emanates from an alarm device located beneath hemodialysis operation unit 120. Further, in the instance that the receiver unit is integrated with an extracorporeal blood treatment system like a hemodialysis system, in response to the signal of a liquid leak, controller 50 can direct the extracorporeal blood operation unit to stop the blood pump(s) and close one or more valves along the liquid line(s) through which blood is drawn from and/or returned to the patient.

The specifications for one specific embodiment of a wetness sensor according to the invention are described below.

WETNESS DETECTOR SYSTEM SPECIFICATIONS

The wireless wetness detector is a small device for the home or clinic that rests on the patient's arm. It detects moisture in the form of blood, saline solution, etc., and signals an alarm condition when blood is present.

The circuitry provides for the monitoring of the presence of blood using a wetness sensor and, optionally an infrared sensor. An optional infrared LED sensor and a wetness sensor are attached to the patient's site gauze. There are two parts: the transmitter unit and the receiver unit. The transmitter unit consists of a sensor and an integrated microcontroller/transmitter. The microcontroller outputs a data stream. The transmitter unit must be FCC approved. The receiver unit obtains power from the functional board.

Wetness Sensor Specifications

Design Features
- Battery powered disposable portable transmitter (>9 months life)
- Shelf life of 1 year with 75% capacity remaining
- Watch size
- ASK (amplitude shift key) transmission, operating on the 433.92 MHz frequency
- UART interface Electronics Subsystem Requirements
- Microcontroller/Transmitter
- Single 3 volt lithium battery power source
- Two (2) GPIO pins
- 433.92 MHz transmit frequency
- Internal 4 MHz RC oscillator
- Sleep mode
- ASK transmitter
- One UART port Microcontroller and Local Peripherals
The selected microcontroller is the Microchip rfPIC12F675F 8-bit microcontroller with an integrated transmitter. The rfPIC12F675F has the following additional features:
- External 13.56 MHz crystal (generates transmitter frequency)
- 64×8 bytes of SRAM data memory
- 128×8 bytes of EEPROM data memory
- 1024×14 words of flash program memory
- four channel 10 bit A/D converter (Min. Vref: 2.5 volts)
- two timers
- data rate up to 40 Kbps
- output power: up to +10 dBm
- power on reset
- ICSP (hardware debugger/flash programming interface)

Transmitter Unit
- A small, wristwatch-sized board has the microcontroller/transmitter circuitry/antenna on one surface and the sensor fingers on the other surface. The circuitry is coated with a suitable potting compound.
- Disposable
- Battery life >9 months
- The transmitter communicates to the receiver using a PCB trace antenna.
- There is a transmission of 7 bytes sent twice in a row every minute for 10 minutes after wetness detected.
- There is a transmission within 3 seconds in the presence of moisture.
- Duration of transmission: approximately 100 msec.
- Low battery detection circuitry alerts the MCU when the battery voltage drops below 2.2 volts during a transmission. Battery contains at least 10% of its life, and the transmitter operates for at least 7 days after the first low battery alarm.
- The transmitter turns on by an initial touching of the wetness sensor surface.
- The transmitter turns off after 10 minutes without wetness detected.
- The transmitter is self-tested by touching the wetness sensor surface, simulating the presence of blood.
- An AD input value over a specified threshold indicates a moisture alarm.
- Unique ID stored in microcontroller's EEPROM.
- Infrared detector to distinguish moisture from blood.

The sensitivity of the sensor wetness grid is determined by the software threshold and the hardware voltage divider. The board contains a 1 Meg ohm resistor from one side of the wetness grid to ground. The other side of the wetness grid is connected to power. To activate the wetness threshold value of 64, 3 Meg ohm or less resistance is required across the wetness grid. With changes to the microcontroller's threshold value, the sensitivity could be adjusted to require as low as 333K ohms across the grid to indicate wetness.

The transmitter supports an infrared emitter and detector to determine if the wetness is caused by blood or perspiration moisture. The different optical properties of blood and water allows this check to determine the cause of wetness detected across the grid.

Radiated emissions and susceptibility testing is performed to ensure the device functions properly in noisy environments, and does not generate interference to other electronic devices in its proximity.

Medical Device Standards of Wetness Sensor
- The device must meet the IEC 60601-1-2 EMC standards for medical devices which includes but is not limited to:
  - IEC 1000-4-2 Electrostatic Discharge (ESD)
  - IEC 1000-4-3 Radiated Susceptibility (RF)
  - FCC Regulations Part 15 section 15.231 (class B device)
  - CISPR 11 Emissions Power Requirements
- Power Source: One 3 volt Lithium coin cell, size: CR2032
- Capacity: 235 mAh nominal. 200 mAh estimated before low battery alarm
- Battery life: 3.3 uA typical standby power. 0.6 ma active power. 120 us active every 3 seconds. Transmitting the message every 1 minute for 100 ms at 8.5 ma, 60 minutes per day yields:
  - Standby Power: 0.0792 mAh/day
  - Active Power: 0.005 mAh/day
  - Transmission: 0.014 mAh/day
  - Battery life=200 mah/0.098 mah/day=2040 days=5.6 years Wetness Sensor Construction
- Material: NEMA GRADE FR-4, 0.062" THK (NOMINAL). 2 oz. Copper finished, UL
- Flammability: Class 94V-0 or Better.
- Finish:
- Plating: tin-lead (50% min., 70% maximum tin) on pads and hole walls only. Pad plating min. 0.0003" THK. Hole wall plating 0.001". Hole sizes after plating. Gold finish on transmitter sensor grid.
- Soldermask: Blue liquid photo imageable (LPI) or SR1000 over bare copper. Soldermask bleed must not extend into holes.
- Silkscreen: Non-conductive white epoxy ink, free of dropouts. Ink should not enter holes or cover pads.
- Warp and Twist: Maximum allowance 0.010" per inch
- Thieving: By discretion and review of design engineer.
- UL Approval/Marking: Required marking is on the solder side. Location is determined by the supplier, but in no case is closer than 0.010" to a conductor or pad.
- Lot identification: Each lot is identified by a lot control mark on the solder side; A date code is acceptable.
- Testing of boards: All PCBs are 100% tested for shorts and opens. A test stamp on each PCB is required.
- QC reporting: Including microsection report and sample, solderability, and cleanliness) and solder sample (may be non-functional board) to accompany each shipment.

Fabrication revision: To be incorporated on solder side tooling in area supplied.

Standards for boards: ANSI/IPC-ML-910 CLASS II standards apply unless otherwise specified.

Layer Structure and Sequence:

4 layers:
  Component side (8 mil trace width)
  Power
  Ground
  Bottom Side (8 mil trace width)

Note: Distance between layers are equal.

High Speed Design Considerations
  Connect power and ground pins with short lengths of 20 mil trace or as wide as pads permit.
  Design antenna trace as required by MCU manufacturer's recommendations.

Antenna Layout:
  The antenna trace is a semicircle with a diameter of approximately 1.058 inches and an entire perimeter of approximately 1/10 of the wavelength, or 2.720 inches. The antenna trace width is 0.079 inches.

Placement
  Place bypass capacitors close to component VDD/GND leads.
  Place the crystal close to the microcontroller and as far away from the antenna as possible.
  The antenna trace is 0.237 inches away from the edge of the transmitter IC and any other traces or components, aside from the tuning components.
  No GND plane underneath the antenna.
  The antenna trace is at least 0.079 inches away from the GND plane and other traces or components.

Receiver Specifications
  The selected receiver is the Micrel MICRF022BM. It can receive transmissions at 433.92 MHz using ASK. Data rates up to 5 kbps can be used. It has a data output that is CMOS compatible. An external 6.7458 MHz crystal is required.

Receiver Unit
  The receiver circuitry is on its own board and interfaces with the functional board via P11 or P33. Zero ohm resistors on the board set connector are used.
  The data from the Data Output pin on the receiver is UART level.
  The functional board recognizes data indicating an alarm condition.
  The receiver board decodes the modulated PWM data.

| P33 | P11 | Receiver |
| --- | --- | --- |
| Pin 1 | T_OUT | 5 volts |
| Pin 3 | 5 volts | T_OUT |
| Pin 9 | GND | GND |

Machine Response—Wetness Detected
  If two messages in a row have wetness value greater than or equal to 16, (exact same wetness value not required), blood alarm.
  Blood alarm stops blood pump, venous clamp closes, audible alarm.
  Alarm message is able to be reset.
  If a wetness detector alarm is reset three times in ten minutes, future wetness detection blood alarms are changed to a warning message.
  A change in the blood sensed status resets the wetness detection back to alarm and resets the 10 minute timer to the beginning state (3 more wetness alarms needed in 10 minutes to go back to warning).

Machine Response—Alarms
  Alarms are generated by the 2008K and 2008K@ home when a condition such as wetness is detected. The alarm for wetness is a serious alarm that wakes a sleeping patient and others in the household. At least one of the following types of warnings is implemented: automatic volume control based upon seriousness of problem on the machine (i.e. needle disconnect causes a high volume alarm), siren, strobe light, or BP cuff could squeeze the arm.

Machine Response—No Communications
  If no message has been received from a wetness detector before the treatment start button is pushed, display "Wetness Detector not Active" message.
  Alarm is reset when wetness detector is found.

Machine Response—Low Battery
  If blood sensed, no low battery warning or alarm.
  If blood not sensed, warning is displayed and is capable of being reset.

Receiver Communication Protocol with >1 Wetness Sensor

Learn Mode
  Learning the IDs of up to 3 wireless wetness detectors is supported by the host machine. All wetness IDs are learned from a service mode screen (2008K and K@home in clinic mode). ID information is saved in the EEPROM for long term storage. The service mode screen supports learning the ID, clearing the ID, and the display of the ID number itself. If the ID is cleared (0) then the ID is not used.

Sequence for Learn:
  Press Wetness detector Learn and CONFIRM. "Wetness Learn Start" is displayed.
  When "Touch and Hold Wetness Detector" is displayed, touch the wetness detector sensor grid.
  When "Release Wetness Detector" is displayed, stop touching the wetness grid. "Wetness Learn Success", "Wetness Learn Failed", "Wetted after Learn" or "Wetted before Learn" is displayed.
  The Wetness Sensor ID is displayed if learn is successful.

Special K@Home mode
  When the K@home is not in clinic mode, it automatically uses the signal from the first 3 wireless wetness detectors it receives. There is no need to do any learning in this mode.

| Communications Protocol | | |
| --- | --- | --- |
| Byte # | Name | Value |
| 0 | HEADER1 | 0xA7 |
| 1 | HEADER2 | 0x35 |
| 2 | ID1 | ID1 |
| 3 | ID2 | ID2 |
| 4 | WETNESS INFO | Bit 0 = 0 if battery ok, 1 if battery low |
| | | Bit 1 = 1 if photo detects blood |
| | | Bit 2-7 = 6 bits of AD wetness data |
| 5 | VERSION | Software version #. If 0, CRC error in hardware |
| 6 | CHECKSUM | 8 bit addition of bytes 0-5 |

The ID is a unique 16-bit non-zero number assigned to the wetness board. Data rate is 1800 bps, 1 start bit, 8 data bits, 1 stop bit, no parity.

A wetness value of 16 or greater indicates a wet condition.

PWM (pulse width modulation) is used to encode the data for the wireless link. The encoding is 66% high for a one, 33% high for a zero. The period is 556 uS.

Receiver Specifications

Power Requirements:
5 Volts: supplied by functional board

Connectors:
UART Port 2×5 pin 0.1" shrouded header

Mechanical Dimensions:
Receiver fits into cabinet. Exact location to be determined.

Transmitter:
1.2"×2.5"×zz"D consists of a printed circuit board conformally coated with potting compound.

Design-For-Test:
Test points are implemented for the Teradyne in-circuit tester at each unique net.

While this invention has been particularly shown and described with references to preferred embodiments thereof, it will be understood by those skilled in the art that various changes in form and details may be made therein without departing from the scope of the invention encompassed by the appended claims.

What is claimed is:

1. A wetness detector system for detecting a liquid leak in an extracorporeal blood treatment system comprising:
    a wetness sensor comprising:
        a solid support comprised of a non-electrically conductive material having first and second surfaces,
        an electronic transmitter on the first surface of said solid support,
        a trace antenna coupled to said electronic transmitter printed on said first surface of said solid support, for sending a signal via said antenna,
        a power source connected to said electronic transmitter,
        an open electric circuit connected to said power source and printed on said second surface of said solid support for detecting the presence of wetness,
        said electric circuit comprised of two electrodes comprised of one or more electrically conductive materials, wherein exposure of said electric circuit of said wetness sensor to moisture closes the electric circuit and generates a detectable electrical signal,
        a microcontroller in communication with said electronic transmitter and said electric circuit, wherein said electrical signal is received by said microcontroller and said microcontroller determines whether the signal is greater than a predetermined wetness detection threshold value, wherein a wetness detection threshold value greater than the predetermined value indicates the presence of a liquid leak, and wherein in response to an indication that a liquid leak has occurred, said microcontroller directs said electronic transmitter to transmit at least one signal that a liquid leak has been detected,
        a voltage detection device coupled to said power source and in communication with said microcontroller for detecting a low power supply of said power source; and
        an attachment device for attaching said wetness sensor to one or more components of the system; and
    a receiver unit integrated with an extracorporeal blood treatment system operation unit, in communication with said wetness sensor comprising:
        a receiver for detecting one or more signal transmissions from said wetness sensor,
        a controller that controls the extracorporeal blood treatment system operation unit, in communication with said receiver, said controller being capable of discontinuing operation of the extracorporeal blood treatment system upon said receiver detecting one or more signal transmissions from said wetness sensor indicating that a liquid leak has occurred, and
        an alert system comprised of one or more alarms selected from the group consisting of the display of a warning message, an audible alarm, and a visual alarm, in communication with said controller, wherein the transmission from the wetness sensor of at least one signal of a liquid leak is received by said receiver of the receiver unit and, in response to said at least one signal, said controller of the receiver unit triggers said alert system, and wherein the receiver unit is in communication with one or more wetness sensors, wherein each of the one or more wetness sensors transmits unique identification information to said receiver of the receiver unit that is recorded by said controller of the receiver unit.

2. The wetness detector system of claim 1, wherein the wetness sensor is attached to one or more liquid lines of the extracorporeal blood treatment system.

3. The wetness detector system of claim 2, wherein the wetness sensor is attached to one or more liquid lines selected from the group consisting of a hydraulic hose, a line for carrying dialysate, and a line for carrying blood.

4. The wetness detector system of claim 1, wherein the wetness sensor is attached to an absorbent material surrounding a needle insertion site.

5. The wetness detector system of claim 1, wherein said microcontroller directs the wetness sensor to enter a low power state for a specified amount of time when no detectable electrical signal is generated during a specific interval of time.

6. The wetness detector system of claim 1, wherein the one or more wetness sensors are further comprised of a wetness sensor receiver and the receiver unit is further comprised of a receiver unit transmitter.

7. The wetness detector system of claim 6, wherein the receiver unit transmitter transmits at every specified interval of time a functionality test signal to the one or more wetness sensors that is received by said wetness sensor receiver and, in response to said signal, the wetness sensor transmits a functionality confirmation signal back to the receiver unit, thereby indicating that the wetness sensor is functional.

8. The wetness detector system of claim 7, wherein the wetness sensor is functional and wherein in response to a lack of transmission of at least one signal of a liquid leak from the one or more wetness sensors during a specific interval of time, the receiver unit transmits a signal to the wetness sensor directing the wetness sensor to enter a low power state for a specified amount of time.

9. The wetness detector system of claim 1, wherein the alert system is reset after one or more selected from the group consisting of the controller is instructed by an external operator to halt the one or more alarms, and moisture is removed from the wetness sensor surface.

10. The wetness detector system of claim 9, wherein the power source of the wetness sensor is one or more batteries.

11. The wetness detector system of claim 10, wherein the microcontroller triggers a low battery alarm when the voltage detected by said voltage detection device is less than a specified voltage, wherein the presence of wetness is not indicated by the wetness sensor.

12. The wetness detector system of claim 11, wherein the low battery alarm is integrated with the receiver unit and is comprised of an audible alarm, a visual alarm or a combination thereof, wherein the low battery alarm differs from the one or more alarms of the alert system.

13. The wetness detector system of claim 12, wherein the microcontroller directs the electronic transmitter to transmit at least one signal to the receiver unit that the voltage of the battery is low and, in response to said at least one signal, the receiver directs the controller to trigger said low battery alarm.

14. The wetness detector system of claim 1, wherein the wetness sensor is further comprised of an illumination device attached to said second surface of the wetness sensor solid support for detecting a presence of blood, the illumination device connected to said power source and in communication with said microcontroller.

15. The wetness detector system of claim 14, wherein the illumination device is comprised of a light emitter and a wavelength-calibrated photodiode detector.

16. The wetness detector system of claim 15, wherein in response to an indication that wetness is present the microcontroller directs the light emitter to produce visible light, wherein a wavelength detected by said photodiode of between about 520 nanometers (nm) and 610 nm indicates that the wetness present is blood.

17. The wetness detector system of claim 15, wherein in response to an indication that wetness is present the microcontroller directs the light emitter to produce near-infrared light, wherein a wavelength detected by said photodiode of between about 740 nm and 820 nm indicates that the wetness present is blood.

18. The wetness detector system of claim 17, wherein in response to a lack of indication that the wetness present is blood during a specific interval of time, the microcontroller directs the wetness sensor to enter a low power state for a specified amount of time.

19. The wetness detector system of claim 18, wherein in response to an indication that the wetness present is blood, said microcontroller directs said electronic transmitter to transmit at least one signal that a needle insertion site blood leak has been detected.

20. A wetness detector system for detecting a liquid leak in an extracorporeal blood treatment system comprising:
one or more wetness sensors each comprising:
a solid support comprised of a non-electrically conductive material having first and second surfaces,
an electronic transmitter on the first surface of said solid support,
a trace antenna coupled to said electronic transmitter printed on said first surface of said solid support,
a power source including one or more batteries connected to said electronic transmitter,
an open electric circuit connected to said power source and printed on said second surface of said solid support for detecting the presence of wetness,
said electric circuit comprised of two electrodes comprised of one or more electrically conductive materials, wherein exposure of said electric circuit of said wetness sensor to moisture closes the electric circuit and generates a detectable electrical signal,
a microcontroller in communication with said electronic transmitter and said electric circuit, wherein said electrical signal is received by said microcontroller and said microcontroller determines whether the signal is greater than a predetermined wetness detection threshold value, wherein a wetness detection threshold value greater than the predetermined value indicates the presence of wetness, and wherein in response to an indication that wetness is present, said microcontroller directs said electronic transmitter to transmit at least one signal that a liquid leak has been detected,
a voltage detection device coupled to said power source and in communication with said microcontroller for detecting a low power supply of said power source, wherein the microcontroller triggers a low battery alarm when the voltage detected by said voltage detection device is less than a specified voltage, wherein the presence of wetness is not indicated by the wetness sensor; and
an attachment device for attaching said wetness sensor to one or more components of the system; and
a receiver unit integrated with an extracorporeal blood treatment system operation unit, the extracorporeal blood treatment selected from the group consisting of oxygenation, detoxification, transfusion, and filtration, in communication with one or more of said wetness sensors,
said receiver unit comprising:
a receiver for detecting one or more signal transmissions from said one or more wetness sensors,
a controller that controls the extracorporeal blood treatment system operation unit, in communication with said receiver, wherein each of the one or more wetness sensors transmits unique identification information to said receiver of the receiver unit that is recorded by said controller of the receiver unit, and
an alert system comprised of one or more alarms selected from the group consisting of the display of a warning message, an audible alarm, and a visual alarm, in communication with said controller, wherein the transmission from the one or more wetness sensors of at least one signal of a liquid leak is received by said receiver of the receiver unit and, in response to said at least one signal, said controller of the receiver unit triggers said alert system and directs the extracorporeal blood treatment system to stop one or more pumps or close one or more blood line valves of the system, and wherein the alert system is reset after one or more selected from the group consisting of the controller resets one or more alarms, and moisture is removed from the wetness sensor surface.

21. The wetness detector system of claim 20, wherein said microcontroller directs the wetness sensor to enter a low power state for a specified amount of time when no detectable electrical signal is generated during a specific interval of time.

22. The wetness detector system of claim 21, wherein the two electrodes of the electric circuit are comprised of one or more electrically conductive materials selected from the group consisting of a metal, polymer, silicon, and carbon.

23. The wetness detector system of claim 22, wherein the low battery alarm is integrated with the receiver unit and is comprised of an audible alarm, a visual alarm or a combination thereof, wherein the low battery alarm differs from the one or more alarms of the alert system.

24. The wetness detector system of claim 23, wherein the microcontroller directs the electronic transmitter to transmit at least one signal to the receiver unit that the voltage of the battery is low and, in response to said at least one signal, the receiver directs the controller to trigger said low battery alarm.

* * * * *